United States Patent [19]
Cellier et al.

[11] Patent Number: 5,457,985
[45] Date of Patent: Oct. 17, 1995

[54] PROCESS FOR MEASURING THE CETANE NUMBER OF SUPPLY FUELS FOR DIESEL ENGINES AND APPARATUS FOR PERFORMING THIS PROCESS

[75] Inventors: Joseph Cellier, Venissieux; Guy Mille, Echalas, both of France; Alex Mottas, Wavre, Switzerland

[73] Assignee: Elf Antar France, Courbevoie, France

[21] Appl. No.: 187,488

[22] Filed: Jan. 28, 1994

[30] Foreign Application Priority Data

Feb. 1, 1993 [FR] France ................. 93 01038

[51] Int. Cl.$^6$ .................................................. G01N 33/22
[52] U.S. Cl. ............................................................. 73/35.02
[58] Field of Search ........................................... 73/35 KR

[56] References Cited

U.S. PATENT DOCUMENTS

| | | |
|---|---|---|
| 3,520,173 | 7/1970 | Hadley . |
| 3,575,039 | 4/1971 | Beal ........................ 73/35 KR |
| 3,678,732 | 7/1972 | Arrigoni et al. ........... 73/35 KR |
| 4,331,024 | 5/1982 | Childs et al. .............. 73/35 KR |
| 4,402,212 | 9/1983 | Childs ....................... 73/35 KR |
| 4,549,883 | 10/1985 | Purcell et al. ............... 44/57 |
| 4,873,947 | 10/1989 | Ryan, III et al. .......... 123/78 C |
| 4,943,303 | 7/1990 | Pialet ........................ 44/57 |
| 5,114,433 | 5/1992 | Dubreux et al. ............ 44/322 |
| 5,114,434 | 5/1992 | Praulus et al. .............. 44/322 |

FOREIGN PATENT DOCUMENTS

| | | |
|---|---|---|
| 0143571 | 6/1985 | European Pat. Off. . |
| 1270838 | 6/1968 | Germany . |

OTHER PUBLICATIONS

Database WPIL Week 8908, Derwent Publ. Ltd., London. AN 89-059996 & SU-A-1 416 910, Aug. 15, 1988.
Database WPIL Week 9144, Derwent Publ. Ltd., London. AN 91-322778 & SU-A-1 608 581, Nov. 23, 1990.

Primary Examiner—Richard E. Chilcot, Jr.
Assistant Examiner—Eric S. McCall
Attorney, Agent, or Firm—Oblon, Spivak, McClelland, Maier & Neustadt

[57] ABSTRACT

An apparatus and method for testing and monitoring fuels produced for diesel engines. The cetane number of a supply fuel for a diesel engine is measured based on the value of the cetane number of two reference fuels. The autoignition delay is measured and compared to the delay for the reference fuels. The delay is measured using a diesel engine which operates at a constant speed with a constant volume compression ratio. The sample of the supply fuel may be drawn and tested in a research laboratory or may be used on line during the production of the fuel.

9 Claims, 3 Drawing Sheets

FIG_2

PROCESS FOR MEASURING THE CETANE NUMBER OF SUPPLY FUELS FOR DIESEL ENGINES AND APPARATUS FOR PERFORMING THIS PROCESS

TECHNICAL FIELD

The present invention relates to a process for measuring the cetane number of supply fuels for diesel engines, as well as to an apparatus for performing this process.

It is used in research and monitoring laboratories, as well as in units for the production of such fuels in installations for the treatment of crude.

PRIOR ART

The cetane number or value of a fuel for a diesel engine represents its ignitability quality. By convention, the cetane numbers of heptamethyl nonane and normal cetane respectively have the values 15 and 100.

One method for determining the cetane number of diesel engine fuels is described in Standard ASTM D613. According to this method, the cetane number of a diesel engine fuel is determined by comparing its autoignition quality with those of mixtures of reference fuels having known cetane numbers.

For the fuel to be analysed and for each reference mixture, the volume compression ratio of the engine is regulated so as to obtain for the fuel to be analysed and for each of the mixtures, a predetermined autoignition delay (13°). In this way are obtained the volume compression ratios of the reference fuels having known values. When the volume compression ratio of the fuel to be analysed is between the volume ratios of the reference mixtures, from this is deduced by interpolation the cetane number of the fuel to be analysed. The measuring equipment used for performing this known method essentially comprises:

a single-cylinder engine having a variable volume compression ratio, a device for measuring the autoignition delay of the fuel able to supply the engine, an injection pump equipped with a micrometer means making it possible to manually regulate the injection lead or advance, a means for indicating the injection lead or advance.

This apparatus must operate under strict operating conditions as defined in ASTM D613.

The volume compression ratio is regulated by means of a plunger, whose position can be modified by manual action on a volume control wheel.

More specifically, in order to determine the cetane number of an engine supply fuel, the engine is successively supplied with two reference fuels having known cetane number values and then by the fuel to be analysed and whose cetane number is to be determined.

According to ASTM D613, the injection advance is regulated to the value 13° before the top dead-centre of the engine piston. For each fuel, the volume compression ratio is manually regulated in order to obtain an autoignition delay value with respect to the injection time (expressed as an angle of the position of the engine crankshaft) equal to 13° and which is read from an autoignition delay indicator.

For each volume ratio regulating operation, the plunger position is noted.

On the basis of these results and the cetane numbers of the reference fuel, the sought cetane number is calculated by interpolation, as indicated hereinbefore.

This method takes a long time to carry out and involves numerous manual operations. It does not make it possible to automatically obtain the cetane number value for engine supply fuels, e.g. in the form of electric signals representing these numbers.

In order to regulate the cetane number value of a fuel being produced, it is necessary to have the same in an almost continuous manner and this is impossible using the method described in ASTM D613.

DESCRIPTION OF THE INVENTION

The present invention aims at obviating this disadvantage and at supplying a process and an apparatus for automatically measuring the cetane numbers of fuels for diesel engines.

This process and this apparatus can be used both in the laboratory for monitoring fuel samples and during the manufacture of a fuel for regulating its cetane number value, by acting on the composition of the mixture constituting said fuel.

To this end, the present invention proposes a process for measuring the value of the cetane number of a supply fuel for diesel engines by comparison with a known value of a cetane number of at least one reference fuel, said supply and reference fuels respectively having autoignition delays, said process consisting of using a measurement diesel engine rotating at a constant speed and successively supplied by said reference fuel and said supply fuel, said measurement engine having a constant compression ratio and a constant injection advance, characterized in that said process consists of calculating the cetane number of the supply fuel on the basis of the value of the cetane number of the reference fuel and on the basis of the respectively measured values of the autoignition delays of the reference fuel and the supply fuel.

According to another feature, the present invention proposes a process, which is characterized in that the measurement engine is successively supplied by two reference fuels having respective known cetane numbers and then by the supply fuel, the value of the cetane number of the supply fuel being calculated by the application of the following formula:

$$Icx = Ic1 + (Ic2 - Ic1)\frac{Dix - Di1}{Di2 - Di1}$$

in which:

Icx is the value of the cetane number of the supply fuel,

Ic1 and Ic2 are respectively the values of the cetane numbers of the reference fuels, Di1 and Di2 are the measured values of the respective autoignition delays of the reference fuels, Dix is the measured value of the autoignition delay of the supply fuel, the reference fuels being chosen in such a way that the value of the cetane number of the supply fuel is between the respective values of the cetane numbers of the reference fuels.

According to another feature, the process according to the invention is characterized in that the measurement engine is supplied during a calibration phase by a reference fuel having a known cetane number and then periodically by a supply fuel during its production and whereof it is wished to know the cetane number value, the cetane number value of the supply fuel being calculated by the application of the following formula:

$$Icx = Ic1 + K(Dix - Di1)$$

in which:

Icx is the value of the cetane number of the supply fuel which is periodically calculated, Ic1 is the known value of the cetane number of the reference fuel, Di1 is the value measured during the calibration phase of the autoignition delay of the reference fuel, Dix is the periodically measured value of the autoignition delay of the supply fuel, K is a constant.

According to another feature, the present invention proposes a process which is characterized in that the diesel engine having a predetermined operating cycle, supply fuel cetane number values are calculated and stored during a measuring cycle corresponding to a plurality of operating cycles, a mean value of the cetane number of the supply fuel being calculated for said measuring cycle on the basis of stored values of said number.

The invention also relates to an apparatus for measuring the cetane number of a supply fuel for diesel engines comprising:

a measuring diesel engine rotating at a constant speed and supplied at a constant flow rate, with a predetermined injection advance or lead, whilst successively receiving the said supply fuel and at least one reference fuel having a known cetane number, said supply and reference fuels respectively having autoignition delays, means for successively supplying the measuring engine with the reference fuel and the supply fuel, a sensor for detecting each fuel injection time into the engine, a sensor for measuring the pressure of the combustion chamber of the engine supplying a pressure measurement signal on an output, means for processing the pressure measurement signal for said reference fuel and for said supply fuel and processing the value of the cetane number of the reference fuel or fuels in order to calculate the value of the cetane number of the supply fuel, characterized in that the processing means comprise:

a circuit for detecting the pressure peak connected to the output of the pressure sensor in order to detect in the output signal of the pressure sensor the time at which a pressure peak appears which corresponds to an autoignition for the reference fuel and for the supply fuel, following the injection time, a measuring circuit connected to an output of the injection sensor and to an output of the pressure peak detection circuit in order to measure the delays separating the injection and pressure peak appearance times, for each of the reference and supply fuels, said delays respectively corresponding to the autoignition delays of said fuels, a processing unit connected to an output of the measuring circuit and to storage means for calculating the value of the cetane number of the supply fuel on the basis of the cetane numbers of the reference fuel and autoignition delays of the reference and supply fuels.

According to a first embodiment, the invention relates to an apparatus which is characterized in that the storage means contain a processing program for calculating the cetane number of the supply fuel by applying the following formula:

$$Icx = Ic1 + (Ic2 - Ic1)\frac{Dix - Di1}{Di2 - Di1}$$

in which:

Icx is the value of the cetane number of the supply fuel,

Ic1 and Ic2 are respectively the values of the cetane numbers of the reference fuels, Di1 and Di2 are the measured values of the respective autoignition delays of the reference fuels, Dix is the measured value of the autoignition delay of the supply fuel.

According to a second embodiment, the invention proposes an apparatus which is characterized in that the storage means contain a processing program for calculating the cetane number of the supply fuel by applying the following formula:

$$Icx = Ic1 + K(Dix - Di1)$$

in which:

Icx is the value of the cetane number of the supply fuel which is periodically calculated, Ic1 is the known value of the cetane number of the reference fuel, Di1 is the value measured during the calibration phase of the autoignition delay of the reference fuel, Dix is the periodically measured value of the autoignition delay of the supply fuel, K is a constant.

According to another feature of the first embodiment, the invention proposes an apparatus which is characterized in that it also comprises:

three tanks for respectively storing two reference fuels having cetane numbers with known predetermined values and a supply fuel having a cetane number whose value is to be measured, the value to be measured being between the predetermined values, three sampling pipes respectively connected to the three outlets of the three tanks and connected to a common engine supply pipe, three controllably opened and closed valves, respectively interposed on the three sampling pipes, said valves having control inlets connected to outputs of the processing unit so that the engine is successively supplied by two reference fuels and by the supply fuel, in order to measure the respective autoignition delays of the reference fuels and the supply fuel for calculating the value of the cetane number of the supply fuel.

According to another feature of the second embodiment, the invention proposes an apparatus which is characterized in that it also has at least two tanks for respectively storing two basic fuels to be mixed in order to constitute a single fuel having a cetane number with a desired value, a tank for storing a reference fuel having a known cetane number, a buffer for successively storing the reference fuel and then samples of the basic fuel mixture, a supply pipe connecting the buffer to the engine supply, two drain pipes respectively connected to two outlets of the basic fuel storage tanks and connected to a common header in which mixing takes place, a sampling pipe connecting said header to the buffer, a reference pipe connecting the outlet of the reference fuel storage tank to an outlet of the buffer, controllably opened and closed valves respectively interposed on the sampling pipes and on the reference pipe, valves for regulating the flow rate of the basic fuel interposed on the drain pipes, the controllably opened and closed valves having control inlets connected to outputs of the processing unit for controlling the filling of the buffer successively by the reference fuel and then by samples of the mixture, the regulating valves having control inlets respectively connected to the outlets of the flow rate regulating means, said regulating means being connected to a measuring output of the processing unit for receiving the measured value of the cetane number of said mixture, said regulating means receiving on another inlet a reference signal corresponding to said desired value of the cetane number of the mixture.

BRIEF DESCRIPTION OF THE DRAWINGS

The invention will be better understood on the basis of the following drawings, wherein show.

DETAILED DESCRIPTION OF THE INVENTION

In general terms, the process and apparatus according to the invention are used for measuring the cetane number of fuels for diesel engines. The cetane number of a fuel is a characteristic of its autoignition, which is itself defined by the autoignition delay or lag of the fuel. This delay is measured between the time of injecting the first drop of fuel into a diesel engine and the time of autoignition, which occurs after a pronounced, sudden pressure rise in the combustion chamber.

Figure 1:
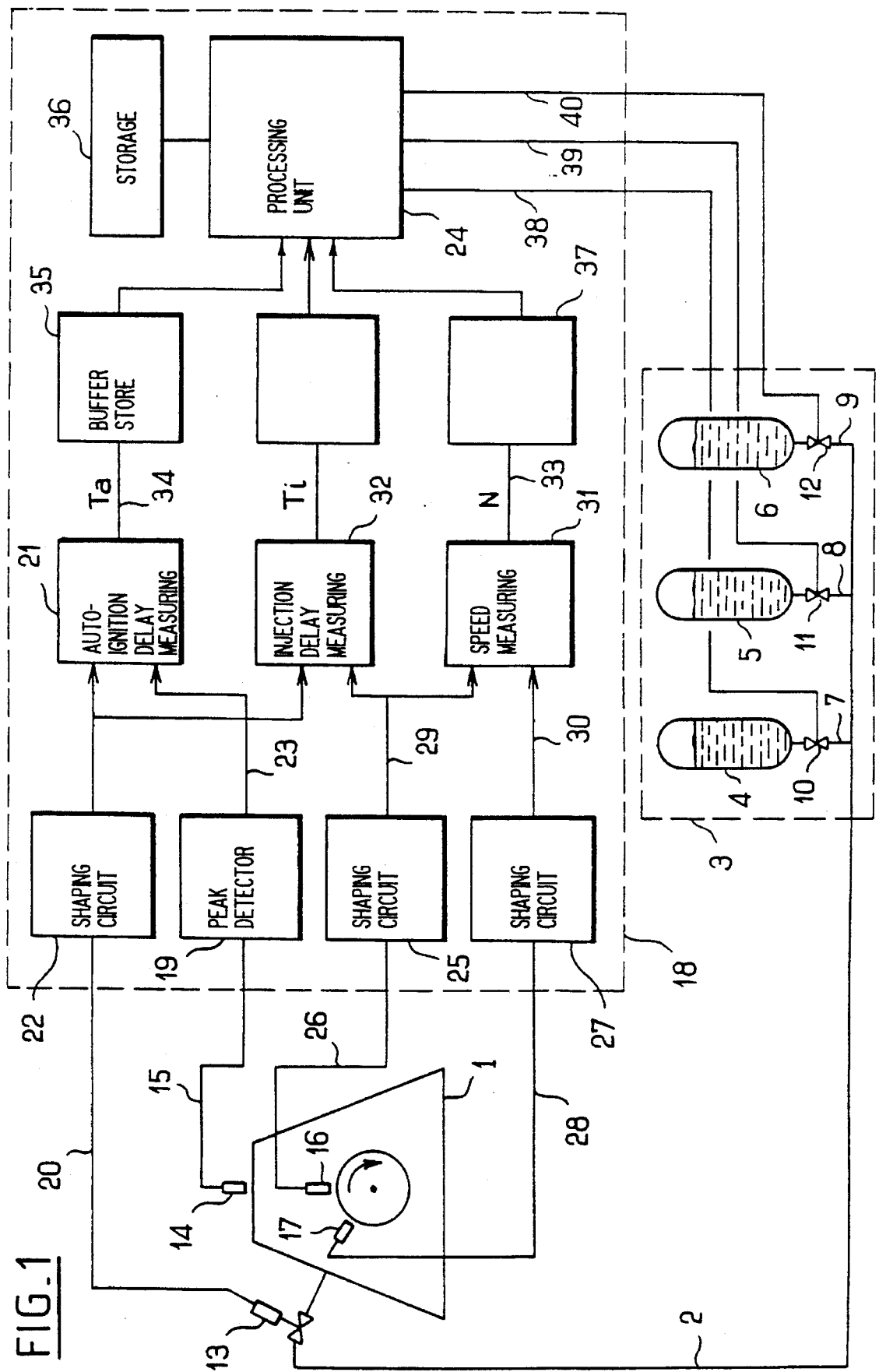
FIG. 1 diagrammatically a first embodiment according to the invention usable in the laboratory for measuring the cetane number of a fuel.

FIG. 1 diagrammatically shows a first embodiment of the apparatus according to the invention usable for carrying out in the laboratory cetane number measurements on fuel samples. The description of said apparatus and its operation will provide a better understanding of the process according to the invention.

The apparatus in this first embodiment comprises a testing or measuring diesel engine 1 supplied with a fuel at a constant flow rate by means of a supply pipe 2. The flow rate can e.g. be 13 ml/mn. The engine rotates at a constant speed of e.g. 900 r.p.m. The injection advance or lead is regulated to a fixed value (e.g. 15° crankshaft) relative to the top dead-centre of the piston of the engine. The measured value of said advance can be displayed by a not shown, digital monitoring indicator located in the vicinity of the engine.

The volume compression ratio of the engine is defined as the ratio between the respective volumes of the combustion chamber when the piston is in the bottom dead-centre and then in the top dead-centre. According to the process of the invention, this ratio is fixed and is regulated manually in known manner using a plunger.

The speed, the supply fuel flow rate, the injection advance and the volume compression ratio of the engine are maintained constant, so that each supply fuel has an autoignition delay representing its autoignition.

The apparatus has means 3 for supplying the engine with at least one reference fuel and the supply fuel. In the first embodiment of the invention said means 3 incorporate three tanks 4,5 and 6 respectively containing the fuel to be analysed and the two reference fuels having known cetane numbers and with respective values Ic1 and Ic2. These tanks are connected to the injection pump of the engine by appropriate pipes 7,8,9, which are themselves connected to the supply pipe 2 by electro-valves 10,11,12. The engine is successively supplied by the three fuels stored in the tanks, by opening and closing electro-valves respectively interposed on the pipes 7,8,9.

The apparatus also has various sensors, namely a sensor 13 for detecting the injection time, which supplies an electric pulse at the time of injecting fuel into the engine, as well as a sensor 14 for measuring the pressure in the combustion chamber and supplying on an output 15 an electric signal representing said pressure.

The apparatus can also have a position sensor 16, which supplies an electrical signal corresponding to the passage of the piston through the top dead-centre, together with a reference position sensor 17 supplying an electrical signal corresponding to the passage of the piston through the position chosen for reference purposes before the top dead-centre (e.g. 13°).

The apparatus also has means 18 for processing the pressure measurement signal supplied by the output 15 of the sensor 14 for the reference fuels and the supply fuel and for the processing of cetane number values of the reference fuels. As will be shown hereinafter, these means make it possible to calculate the value of the cetane number of the supply fuel supplied by the pipe 2.

The processing means 18 in this first embodiment are constituted by the following:

A circuit 19 for detecting the pressure peak connected to the output 15 of the pressure sensor 14 in order to detect in said output signal of said sensor, the time at which a pressure peak appears. This peak corresponds to the autoignition of the fuel supplied to the engine, following the injection time. This injection time is determined by the output signal of the injection sensor 13, said signal being supplied by an output 20 of said sensor 13.

A measuring circuit 21 is connected to the output 20 of the injection sensor, e.g. by means of a circuit 22 for shaping the signal supplied by the output 20 of the injection sensor 13. The measuring circuit is also connected to an output 23 of the detection circuit 19, which supplies a signal representing the time at which the pressure peak appears in the combustion chamber for each fuel. The circuit 21 makes it possible to measure the delay separating the injection time and the pressure peak appearance time, for the reference fuels and the supply fuel supplied to the engine. These delays respectively correspond to the autoignition delays of said fuels.

A processing unit 24 is connected to the output 34 of the measuring circuit 21 for the autoignition delay by means of a buffer store 35. This processing unit is also connected to storage means 36. It makes it possible to calculate the values of the cetane numbers of the supply fuel on the basis of the cetane numbers of the reference fuels and the values of the autoignition delays of the reference and supply fuels.

According to the first embodiment, the storage means 36 of the processing unit 24 contain a processing program for calculating the cetane number of the supply fuel by applying the following formula:

$$Icx = Ic1 + (Ic2 - Ic1) \frac{Dix - Di1}{Di2 - Di1}$$

in which:

Icx is the value of the cetane number of the supply fuel,

Ic1 and Ic2 are respectively the values of the cetane numbers of the reference fuels, Di1 and Di2 are the measured values of the respective autoignition delays of the reference fuels, Dix is the measured value of the autoignition delay of the supply fuel.

It is also possible to see the following in FIG. 1:

a shaping circuit 25, which receives the signal 26 from the top dead-centre sensor 16 and which supplies on an output 29 an electric pulse signal representing the passage time of the piston at the dead-centre, a shaping circuit 27, which receives the signal 28 from the reference sensor 17 and which supplies on an output 30 an electric pulse signal representing the passage time of the piston to the reference position (e.g. 13°), a speed measuring circuit 31 connected to the outputs 29 and 30 and which calculates the speed of the engine and supplies a measurement signal 33 for said speed, an injection delay measuring circuit 32 connected to the top dead-centre output 29 and to the injection time output 20, said circuit calculating the injection advance delay and supplying to an output 34, a measurement signal for said delay.

According to the first embodiment of the invention, the apparatus also has a sampling system 3 incorporating the following components:

two tanks 4,5 respectively containing two reference fuels with known cetane numbers of values Ic1 and Ic2, said fuels being chosen in such a way that their cetane number values surround the value of the cetane number of the fuel to be analysed, a tank 6 containing the fuel to be analysed, three sampling pipes 7,8,9 respectively connected to the three outlets of the three tanks 4,5,6 and connected to a common engine supply pipe 2, three controllably openable and closable electrovalves 10,11,12 interposed respectively on the three sampling pipes, said electrovalves having control inlets connected to the outputs 38,39,40 of the processing unit.

The program of the processing unit 24 stored in the storage means 36 takes place in such a way that the engine 1 is successively supplied by the two reference fuels and by the fuel to be analysed during predetermined periods, e.g. of 120 seconds each.

For each engine cycle, the autoignition delay measuring circuit 21 calculates the said delay, whose value is then recorded in the buffer store 35. Thus, a plurality of values are obtained for the autoignition delays of the reference fuels and the fuel to be analysed and these are processed by the processing unit 24 in accordance with the formula given hereinbefore.

Figure 2:
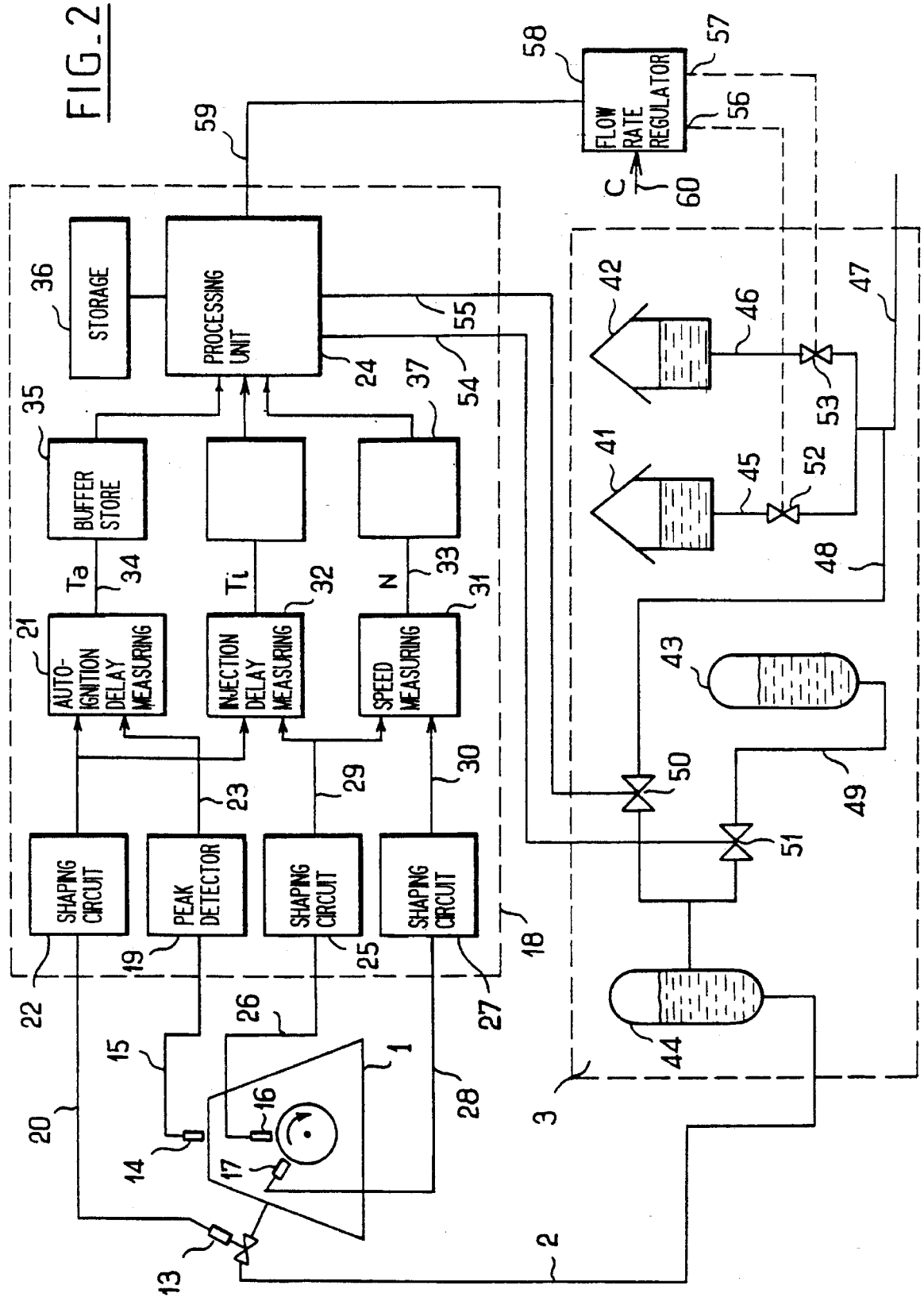
FIG. 2 diagrammatically a second embodiment according to the invention for on-line measurement and regulating the cetane number of a fuel being manufactured.

FIG. 2 diagrammatically shows a second embodiment of the apparatus according to the invention usable for continuously carrying out the measurement of the value of the cetane number of a fuel being manufactured. This measurement is then used for regulating the cetane number value of the manufactured fuel to a predetermined reference or desired value.

The apparatus according to the second embodiment comprises a measuring or test diesel engine 1 equipped with injection time and pressure sensors 13,14 respectively, as described for the first embodiment and operating under the same conditions, as well as means 18 for processing signals supplied by said sensors, as described for the first embodiment. As in the first embodiment, a program is recorded in the storage means 36. The program particular to said second embodiment enables the processing unit to perform calculations and supply controls, as will become apparent hereinafter. The processing unit 24 also has an output 59 supplying an analog signal 59 representative of the value of the cetane number of the fuel being manufactured.

According to the second embodiment, the engine supply means 3 are constituted by the following components:

at least two tanks 41,42 for storing two basic fuels to be mixed in order to form a single fuel having a cetane number of a desired value, a tank 43 for storing a reference fuel having a cetane number with a known value, a buffer 44 for successively storing a reference fuel sample at the start of the operation and then samples of the mixture of the basic fuels, a supply pipe 2 connecting the buffer to the engine supply, two drain pipes 45,46 respectively connected to the two outlets of the basic fuel storage tanks 41,42 and connected to a common header 47 in which the desired mixing takes place, a sampling pipe 48 connecting the header 47 to the buffer 44, a reference pipe 49 connecting the outlet of the reference fuel storage tank to an inlet of the buffer, controllably opened and closed electrovalves 50,51 respectively interposed on the sampling pipes 48 and on the reference pipe 49, valves 52,53 for regulating the flow rate of the basic fuels located on the drain pipes 45,46.

The controlled opening and closing electrovalves 50,51 have control inlets connected to outputs 54,55 of the processing unit in order to control the filling of the buffer, successively with the reference fuel and with the samples of the mixture. The regulating valves 52,53 have control inlets respectively connected to the outlets 56,57 of the flow rate regulating means 58, said regulating means being connected to a measuring output 59 of the processing unit in order to receive the measured value of the cetane number of the mixture, said regulating means receiving on another input 60 a reference signal corresponding to the desired value for the cetane number of the mixture.

According to this second embodiment, during a first phase preceding fuel manufacture, the buffer 44 is filled with reference fuel by opening the electrovalve 51, the electrovalve 50 being closed. The engine 1 is then supplied for a predetermined time, e.g. 120 seconds, during which the autoignition delay of the reference fuel is determined by the processing means 18.

When this calibration operation is at an end, the buffer 44 is emptied and is then filled with a sample of fuel being manufactured and which is sampled in the header 17 by opening the electrovalve 50 and closing the electrovalve 51.

The engine is supplied with a sample of the fuel being manufactured for a predetermined time, e.g. 120 seconds, the processing means 18 measuring the autoignition delay of said fuel sample and calculating the value of its cetane number by applying the following formula:

$$Icx = Ic1 + K(Dix - Di1)$$

in which:

Icx is the value of the cetane number of the fuel being manufactured,

Ic1 is the known value of the cetane number of the reference fuel,

Di1 is the value of the autoignition delay of the reference fuel measured during the calibration phase, Dix is the measured value of the autoignition delay of the fuel being manufactured, K is a constant.

The buffer 44 is emptied and then filled with a new sample of fuel being manufactured and a new analysis cycle takes place. The operation is repeated until the end of the manufacture of the desired fuel quantity.

The analog signal 59 supplied by the output of the processing unit 24 is representative. This value of the cetane number of the fuel being manufactured is compared by regulating means 58 with the desired value 60 for the cetane number of the manufactured fuel. These regulating means 58 supply electric signals on outputs 56,57 for controlling the opening and closing of the valves 52,53, so that the variation between the desired value and the measured value of the cetane number is zero.

According to the two embodiments, the processing unit has display means not shown in FIGS. 1 and 2 making it possible to display the value of the cetane number of the reference fuels and the fuel to be analysed, together with other parameters. Reference is e.g. made to the rotation speed of the engine, the analysis time, the autoignition delays of the reference and supply fuels and the injection lead.

Figure 3:
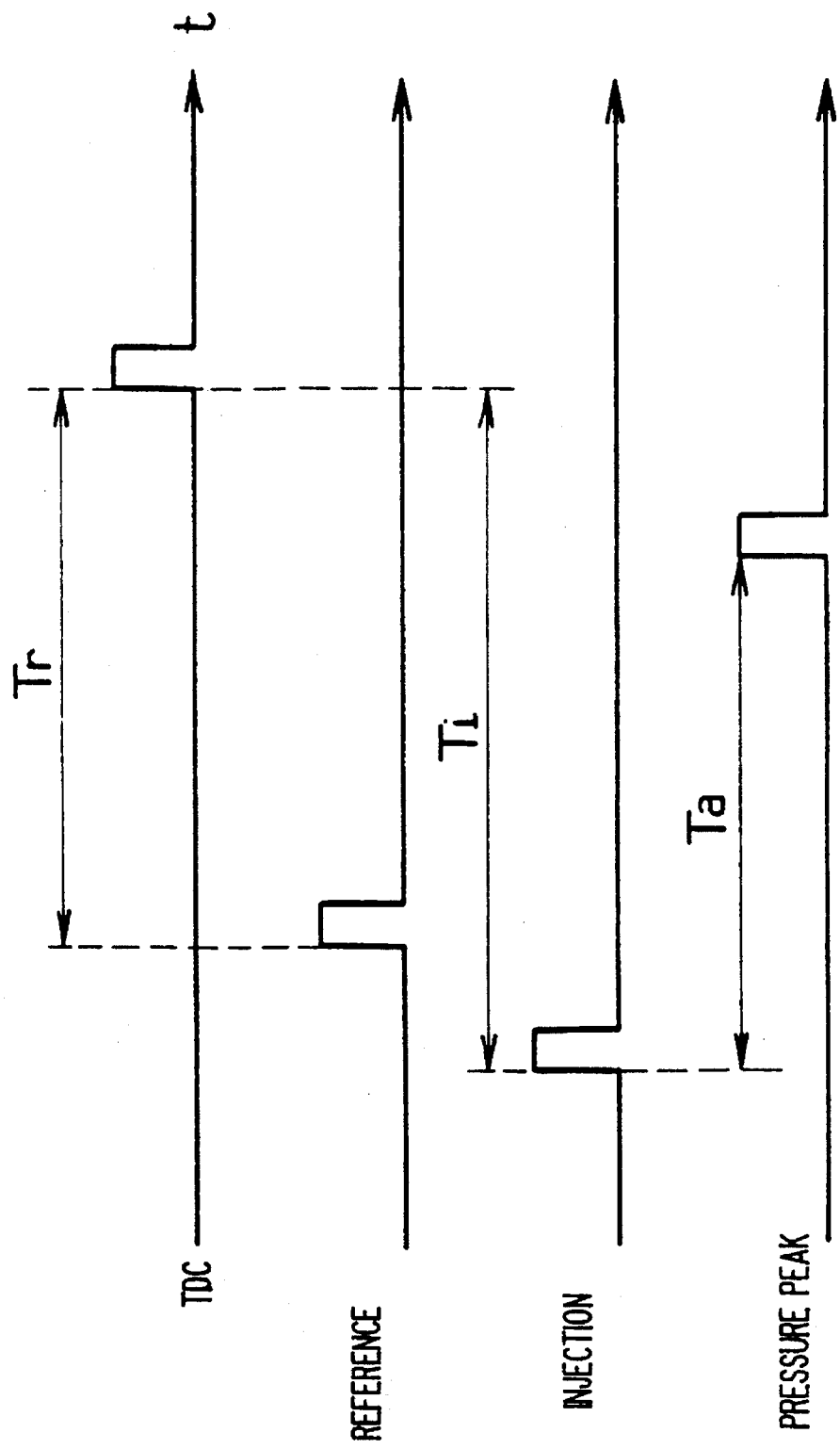
FIG. 3 a timing diagram of the essential signals used in the apparatuses of FIGS. 1 and 2.

FIG. 3 is a timing diagram of the essential signals in the apparatuses diagrammatically shown in FIGS. 1 and 2.

The time interval $T_i$ separating the injection start signal from the top dead-centre signal (TDC) represents the injection lead.

The time interval $T_a$ separating the start of the injection signal from the start of the pressure peak signal represents the autoignition delay of the fuel supplying the engine.

The time interval $T_r$ separating the reference position pulse from the top dead-centre position pulse is constant when the engine rotates at a constant speed. This value $T_r$ makes it possible to calculate the engine rotation speed.

We claim:

1. Process for measuring a value of a cetane number of a supply fuel for diesel engines by comparison with a known value of a cetane number of at least one reference fuel, said supply and reference fuels respectively having autoignition delays, said processes consisting of using a measurement diesel engine rotating at a constant speed and successively supplied by said reference fuel and said supply fuel, said measurement engine having a constant compression ratio and a constant injection advance, characterized in that said process consists of calculating the cetane number of the supply fuel based on the value of the cetane number of the reference fuel and the respectively measured values of the autoignition delays of the reference fuel and the supply fuel.

2. Process according to claim 1, characterized in that the measurement engine is successively supplied by two reference fuels having respective known cetane numbers and then by the supply fuel, the value of the cetane number of the supply fuel being calculated by:

$$Icx = Ic1 + (Ic2 - Ic1)\frac{Dix - Di1}{Di2 - Di1}$$

in which:

Icx is the value of the cetane number of the supply fuel,

Ic1 and Ic2 are respectively the values of the cetane numbers of the reference fuels, Di1 and Di2 are the measured values of the respective autoignition delays of the reference fuels, Dix is the measured value of the autoignition delay of the supply fuel, the reference fuels being chosen in such a way that the value of the cetane number of the supply fuel is between the respective values of the cetane numbers of the reference fuels.

3. Process according to claim 1, characterized in that the measurement engine is supplied during a calibration phase by a reference fuel having a known cetane number and then periodically by a supply fuel during its production and whereof it is wished to know the cetane number value, the cetane number value of the supply fuel being calculated by:

$$Icx = Ic1 + K(Dix - Di1)$$

in which:

Icx is the value of the cetane number of the supply fuel which is periodically calculated, Ic1 is the known value of the cetane number of the reference fuel, Di1 is the value measured during the calibration phase of the autoignition delay of the reference fuel, Dix is the periodically measured value of the autoignition delay of the supply fuel, K is a constant.

4. Process according to either of claims 2 or 3, characterized in that the diesel engine has a predetermined operating cycle, supply fuel cetane number values are calculated and stored during a measuring cycle corresponding to a plurality of operating cycles, a mean value of the cetane number of the supply fuel is calculated for said measuring cycle based on stored values of said number.

5. Apparatus for measuring a cetane number of a supply fuel for diesel engines comprising:

a measuring diesel engine rotating at a constant speed and supplied at a constant flow rate, with a predetermined injection advance or lead, while successively receiving said supply fuel and at least one reference fuel having a known cetane number, said supply and reference fuels respectively having autoignition delays, means for successively supplying the measuring engine with the reference fuel and the supply fuel, a sensor for detecting each fuel injection time into the engine, a sensor for measuring pressure of a combustion chamber of the engine and supplying a pressure measurement signal on an output, means for processing the pressure measurement signal for said reference fuel and for said supply fuel and processing a value of a cetane number of the reference fuel in order to calculate a value of the cetane number of the supply fuel, characterized in that the processing means comprises:

a circuit for detecting a pressure peak, connected to the output of the pressure sensor, in order to detect in the pressure measurement signal the time at which a pressure peak appears which corresponds to an autoignition for the reference fuel and for the supply fuel, following the injection time, a measuring circuit connected to an output of the injection sensor and to an output of the a pressure peak detection circuit in order to measure the delays separating the injection and pressure peak appearance times, for each of the reference and supply fuels, said delays respectively corresponding to the autoignition delays of said fuels a processing unit connected to an output of the measuring circuit and to storage means for calculating the value of the cetane number of the supply fuel based on the cetane numbers of the reference fuel and autoignition delays of the reference and supply fuels.

6. Apparatus according to claim 5, characterized in that the storage means contain a processing program for calculating the cetane number of the supply fuel by:

$$Icx = Ic1 + (Ic2 - Ic1)\frac{Dix - Di1}{Di2 - Di1}$$

in which:

Icx is the value of the cetane number of the supply fuel,

Ic1 and Ic2 are respectively values of cetane numbers of the reference fuels,

Di1 and Di2 are measured values of respective autoignition delays of the reference fuels, Dix is a measured value of the autoignition delay of the supply fuel.

7. Apparatus according to claim 5, characterized in that the storage means contain a processing program for calculating the cetane number of the supply fuel by:

$$Icx = Ic1 + K(Dix - Di1)$$

in which:

Icx is a value of the cetane number of the supply fuel which is periodically calculated, Ic1 is a known value of the cetane number of the reference fuel, Di1 is a value measured during a calibration phase of the autoignition delay of the reference fuel, Dix is a periodically measured value of an autoignition delay of the supply fuel, K is a constant.

8. Apparatus according to claim 6, characterized in that it also comprises:

three tanks for respectively storing two reference fuels having cetane numbers with known predetermined values and a supply fuel having a cetane number whose value is to be measured, the value to be measured being between the predetermined values, three sampling pipes respectively connected to three outlets of the three tanks and connected to a common engine supply pipe, three controllably opened and closed valves, respectively interposed on the three sampling pipes, said valves having control inlets connected to outputs of the processing unit so that the engine is successively supplied by two reference fuels and by the supply fuel, in order to measure the respective autoignition delays of the reference fuels and the supply fuel for calculating the value of the cetane number of the supply fuel.

9. Apparatus according to claim 7, characterized in that it also has at least two tanks for respectively storing two basic fuels to be mixed in order to constitute a single fuel having a cetane number with a desired value, a tank for storing a reference fuel having a known cetane number, a buffer for successively storing the reference fuel and then samples of the basic fuel mixture, a supply pipe connecting the buffer to the engine supply, two drain pipes respectively connected to two outlets of the basic fuel storage tanks and connected to a common header in which mixing takes place, a sampling pipe connecting said head to the buffer, a reference pipe connecting the outlet of the reference fuel storage tank to an outlet of the buffer, controllably opened and closed valves respectively interposed on the sampling pipes and on the reference pipe, valves for regulating the flow rate of the basic fuel interposed on the drain pipes, the controllably opened and closed valves having control inlets connected to outputs of the processing unit for controlling filling of the buffer successively by the reference fuel and then by samples of the mixture, the regulating valves having control inlets respectively connected to the outlets of the flow rate regulating means, said regulating means being connected to a measuring output of the processing unit for receiving the measured value of the cetane number of said mixture, said regulating means receiving on another inlet a reference signal corresponding to said desired value of the cetane number of the mixture.

* * * * *